United States Patent
Soltis

(10) Patent No.: US 8,639,355 B2
(45) Date of Patent: Jan. 28, 2014

(54) INSULATION AND STABILITY FEATURES FOR AN IMPLANTABLE MEDICAL DEVICE LEAD

(75) Inventor: Brian D. Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/532,368

(22) Filed: Jun. 25, 2012

(65) Prior Publication Data

US 2013/0013045 A1 Jan. 10, 2013

Related U.S. Application Data

(60) Provisional application No. 61/505,208, filed on Jul. 7, 2011.

(51) Int. Cl.
*A61N 1/36* (2006.01)

(52) U.S. Cl.
USPC .......................................................... 607/118

(58) Field of Classification Search
USPC .......................................................... 607/118
See application file for complete search history.

(56) References Cited

U.S. PATENT DOCUMENTS

| | | |
|---|---|---|
| 4,573,481 A | 3/1986 | Bullara |
| 4,590,949 A | 5/1986 | Pohndorf |
| 4,602,624 A | 7/1986 | Naples et al. |
| 4,740,170 A | 4/1988 | Lee et al. |
| 4,920,979 A | 5/1990 | Bullara |
| 4,979,511 A | 12/1990 | Terry, Jr. |
| 5,095,905 A | 3/1992 | Klepinski |
| 5,218,089 A | 6/1993 | Mariotti et al. |
| 5,251,634 A | 10/1993 | Weinberg |
| 5,324,322 A | 6/1994 | Grill, Jr. et al. |
| 5,334,438 A | 8/1994 | Saugnac |
| 5,351,394 A | 10/1994 | Weinberg |
| 5,505,201 A | 4/1996 | Grill et al. |
| 5,531,778 A | 7/1996 | Maschino et al. |
| 5,674,272 A | 10/1997 | Bush et al. |

(Continued)

FOREIGN PATENT DOCUMENTS

| | | |
|---|---|---|
| WO | WO2006093685 A1 | 9/2006 |
| WO | WO2007024164 A1 | 1/2007 |

(Continued)

OTHER PUBLICATIONS

International Search Report and Written Opinion Issued in PCT/US2009/063442, mailed Feb. 1, 2010, 11 pages.

(Continued)

*Primary Examiner* — George Manuel
(74) *Attorney, Agent, or Firm* — Faegre Baker Daniels LLP

(57) ABSTRACT

A lead assembly for an implantable medical device includes a lead body having a proximal end and a distal end. A length of the lead body extends from the proximal end to the distal end and a width of the lead body is transverse to the length. One or more electrodes are disposed proximate a distal end of the lead body. One or more insulative elements are coupled to the one or more electrodes to insulate a first portion of the one or more electrodes such that a second portion of the one or more electrodes is exposed for delivering electrical signals. The one or more insulative elements each have a width greater than the width of the lead body.

20 Claims, 4 Drawing Sheets

(56) References Cited

U.S. PATENT DOCUMENTS

| | | | |
|---|---|---|---|
| 5,689,877 A | 11/1997 | Grill et al. | |
| 5,782,892 A | 7/1998 | Castle et al. | |
| 5,964,702 A | 10/1999 | Grill et al. | |
| 6,038,479 A | 3/2000 | Werner et al. | |
| 6,051,017 A | 4/2000 | Loeb et al. | |
| 6,093,197 A | 7/2000 | Bakula et al. | |
| 6,178,349 B1 | 1/2001 | Kieval | |
| 6,249,708 B1 | 6/2001 | Nelson et al. | |
| 6,292,703 B1 | 9/2001 | Meier et al. | |
| 6,600,956 B2 | 7/2003 | Maschino et al. | |
| 6,725,096 B2 | 4/2004 | Chinn et al. | |
| 7,047,081 B2 | 5/2006 | Kuzma | |
| 7,160,298 B2 | 1/2007 | Lawew et al. | |
| 7,212,867 B2 | 5/2007 | Van Venrooij et al. | |
| 7,561,923 B2 | 7/2009 | Libbus et al. | |
| 7,807,925 B2 | 10/2010 | Zarembo | |
| 7,831,311 B2 | 11/2010 | Cross, Jr. et al. | |
| 7,925,358 B2 * | 4/2011 | Belden et al. | 607/122 |
| 7,933,662 B2 | 4/2011 | Marshall et al. | |
| 2003/0040785 A1 | 2/2003 | Maschino et al. | |
| 2004/0010303 A1 | 1/2004 | Bolea et al. | |
| 2004/0111139 A1 | 6/2004 | McCreery | |
| 2006/0122675 A1 | 6/2006 | Libbus et al. | |
| 2006/0259078 A1 | 11/2006 | Libbus | |
| 2007/0118177 A1 | 5/2007 | Libbus et al. | |
| 2007/0142871 A1 | 6/2007 | Libbus et al. | |
| 2007/0203556 A1 | 8/2007 | Rutten et al. | |
| 2007/0255320 A1 | 11/2007 | Inman et al. | |
| 2008/0051839 A1 | 2/2008 | Libbus et al. | |
| 2008/0058871 A1 | 3/2008 | Libbus et al. | |
| 2008/0058874 A1 | 3/2008 | Westlund et al. | |
| 2008/0058901 A1 | 3/2008 | Ternes et al. | |
| 2008/0086181 A1 | 4/2008 | Amurthur et al. | |
| 2008/0091255 A1 | 4/2008 | Caparso et al. | |
| 2008/0103407 A1 | 5/2008 | Bolea et al. | |
| 2008/0103545 A1 | 5/2008 | Bolea et al. | |
| 2008/0172101 A1 | 7/2008 | Bolea et al. | |
| 2008/0177365 A1 | 7/2008 | Bolea et al. | |
| 2008/0183258 A1 | 7/2008 | Inman | |
| 2008/0195188 A1 | 8/2008 | Libbus et al. | |
| 2008/0234780 A1 | 9/2008 | Smith et al. | |
| 2009/0048641 A1 | 2/2009 | Libbus | |
| 2009/0210042 A1 | 8/2009 | Kowalczewski | |
| 2009/0275997 A1 | 11/2009 | Faltys et al. | |
| 2010/0036451 A1 | 2/2010 | Hoffer | |
| 2010/0121405 A1 | 5/2010 | Ternes et al. | |
| 2010/0305674 A1 | 12/2010 | Zarembo et al. | |
| 2010/0331938 A1 | 12/2010 | Sommer et al. | |
| 2011/0004281 A1 | 1/2011 | Jones | |
| 2011/0022142 A1 | 1/2011 | Barker et al. | |
| 2012/0065702 A1 | 3/2012 | Arcot-Krishnamurthy et al. | |
| 2013/0005169 A1 | 1/2013 | Soltis et al. | |

FOREIGN PATENT DOCUMENTS

| | | |
|---|---|---|
| WO | WO2008088798 A1 | 7/2008 |
| WO | WO2009025817 A2 | 2/2009 |
| WO | WO2011053766 A1 | 5/2011 |

OTHER PUBLICATIONS

International Search Report and Written Opinion Issued in PCT/US2010/026350, mailed Jun. 2, 2010.

International Search Report and Written Opinion Issued in PCT/US2011/049585, mailed Dec. 19, 2011.

International Search Report and Written Opinion Issued in PCT/US2012/044020, mailed Sep. 11, 2012, 9 pages.

International Search Report and Written Opinion issued in PCT/US2012/044028, mailed Oct. 1, 2012, 9 pages.

* cited by examiner

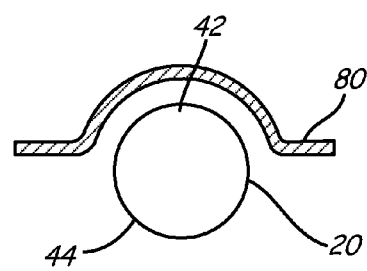
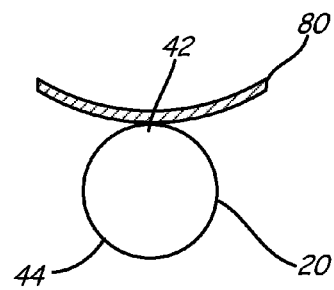
FIG. 5A  FIG. 5B
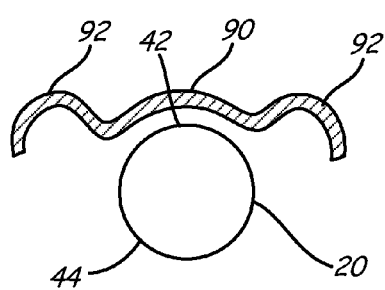
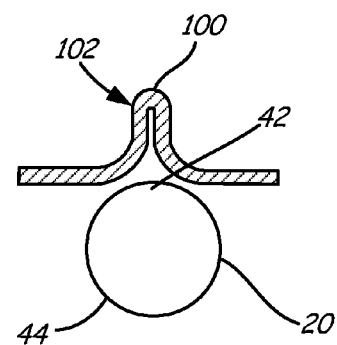
FIG. 5C  FIG. 5D

INSULATION AND STABILITY FEATURES FOR AN IMPLANTABLE MEDICAL DEVICE LEAD

CROSS-REFERENCE TO RELATED APPLICATION

This application claims priority to Provisional Patent Application No. 61/505,208, filed Jul. 7, 2011, which is herein incorporated by reference in its entirety.

TECHNICAL FIELD

The present invention relates to medical devices. More specifically, the invention relates to insulation and stability features for implantable medical device leads.

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or laid next to the nerve. The lead should be configured so that the electrodes remain in contact with the nerve to be stimulated

SUMMARY

Discussed herein are insulative elements for a medical device lead that are configured to direct stimulation toward tissue to be stimulated and provide lead stability, as well as medical device leads including such insulative elements.

In Example 1, a lead assembly for an implantable medical device includes a lead body having a proximal end and a distal end. A length of the lead body extends from the proximal end to the distal end and a width of the lead body is transverse to the length. One or more electrodes are disposed proximate a distal end of the lead body. One or more insulative elements are coupled to the one or more electrodes to insulate a first portion of the one or more electrodes such that a second portion of the one or more electrodes is exposed for delivering electrical signals. The one or more insulative elements each have a width greater than the width of the lead body.

In Example 2, the lead assembly according to Example 1, wherein the width of the one or more insulative elements is at least about 1.5 times the width of the lead body.

In Example 3, the lead assembly according to either Example 1 or 2, wherein the one or more insulative elements extend beyond the width of the lead body by more than 1.0 mm.

In Example 4, the lead assembly according to any of Examples 1-3, wherein the one or more insulative elements are comprised of a flexible material.

In Example 5, the lead assembly according to any of Examples 1-4, wherein insulative elements are collapsible during implantation, and wherein the insulative elements extend to an uncollapsed state after implantation.

In Example 6, the lead assembly according to any of Examples 1-5, wherein each of the one or more insulative elements is associated with one of the one or more electrodes.

In Example 7, the lead assembly according to any of Examples 1-6, wherein at least one of the one or more insulative elements is coupled to more than one of the one or more electrodes.

In Example 8, a lead assembly for an implantable medical device includes a lead body having a proximal end, a distal end, a length that extends between the proximal end and distal end, and a width transverse to the length. One or more conductors extend through the lead body and are configured for connection to a pulse generator. One or more electrodes at the distal end of the lead body, which are configured for placement adjacent to tissue to be stimulated, are electrically coupled to the one or more conductors. One or more insulative elements are coupled to the one or more electrodes and cover a portion of the one or more electrodes and each have a width greater than the width of the lead body.

In Example 9, the lead assembly according to Example 8, wherein the width of the one or more insulative elements is at least about 1.5 times the width of the lead body.

In Example 10, the lead assembly according to either Example 8 or 9, wherein the one or more insulative elements extend beyond the width of the lead body by more than 1.0 mm.

In Example 11, the lead assembly according to any of Examples 8-10, wherein the one or more insulative elements are comprised of a flexible material.

In Example 12, the lead assembly according to any of Examples 8-11, wherein insulative elements are collapsible during implantation, and wherein the insulative elements extend to an uncollapsed state after implantation.

In Example 13, the lead assembly according to any of Examples 8-12, wherein each of the one or more insulative elements is associated with one of the one or more electrodes.

In Example 14, the lead assembly according to any of Examples 8-13, wherein at least one of the one or more insulative elements is coupled to more than one of the one or more electrodes.

In Example 15, a lead assembly for an implantable medical device includes a lead body having a proximal end and a distal end. A length of the lead body extends from the proximal end to the distal end and a width of the lead body is transverse to the length. One or more electrodes are disposed proximate a distal end of the lead body, and one or more insulative elements coupled to the one or more electrodes such that, when the lead assembly is implanted, the one or more insulative elements are on a side of the lead body opposite tissue to be stimulated. The one or more insulative elements each have a width greater than the width of the lead body such that portions of the insulative elements extend beyond the periphery of the lead body.

In Example 16, the lead assembly according to Example 15, wherein the width of the one or more insulative elements is at least about 1.5 times the width of the lead body.

In Example 17, the lead assembly according to either Example 15 or 16, wherein the one or more insulative elements are comprised of a flexible material.

In Example 18, the lead assembly according to any of Examples 15-17, wherein insulative elements are collapsible during implantation, and wherein the insulative elements extend to an uncollapsed state after implantation.

In Example 19, the lead assembly according to any of Examples 15-18, wherein each of the one or more insulative elements is associated with one of the one or more electrodes.

In Example 20, the lead assembly according to any of Examples 15-19, wherein at least one of the one or more insulative elements is coupled to more than one of the one or more electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 5A-5D are cross-sectional views of electrodes and embodiments of attached insulative stability features.

Figure 1:
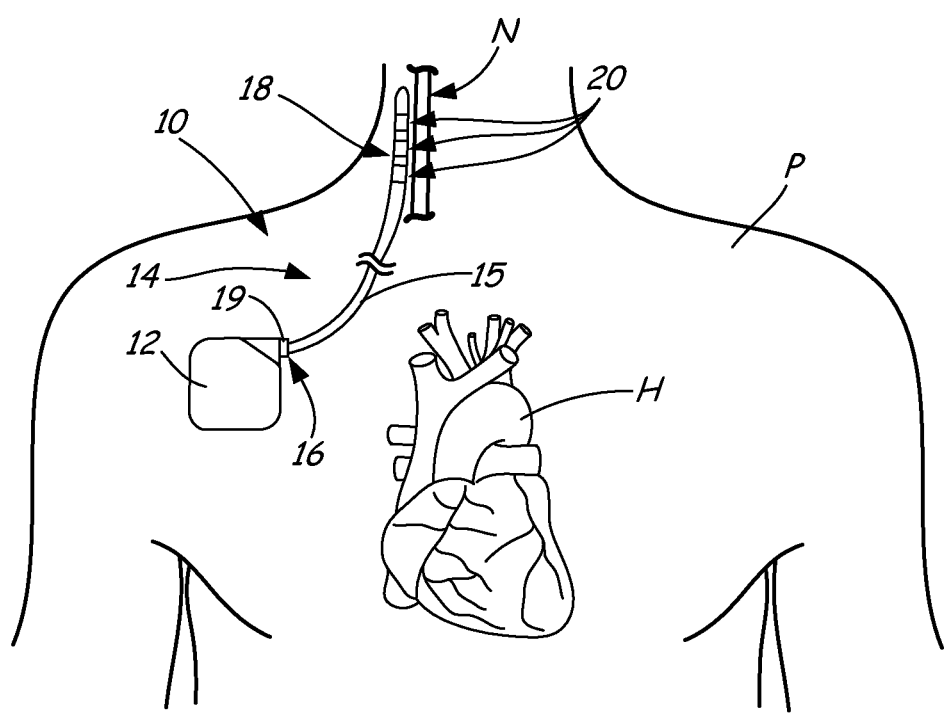
FIG. 1 is an embodiment of a neurostimulation system according to the present invention and portions of an environment in which the neurostimulation system is used.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows an embodiment of a neurostimulation system 10 according to the present invention implanted in a patient P. The neurostimulation system 10 includes an implantable medical device (IMD) 12 with a lead 14 including a lead body 15 and having a proximal end 16 and a distal end 18. In one embodiment, the IMD 12 includes a pulse generator. The IMD 12 can be implanted subcutaneously within the body, typically at a location such as in a patient's chest or abdomen, although other implantation locations are possible. The proximal end 16 of the lead 14 can be coupled to the IMD 12 via one or more connectors 19. Alternatively, the lead 14 may be formed integrally with the IMD 12. The distal end 18 of the lead 14, in turn, can be implanted at a desired location in the patient's body to stimulate excitable tissue.

The distal end 18 of the lead 14 includes a plurality of electrodes 20. The electrodes 20 are electrically connected to the IMD 12 via one or more conductors (not shown in FIG. 1) extending through the lead 14. In some embodiments, the electrodes 20 include conductive bands that extend around the distal end 18 of the lead 14. The electrodes 20 are positioned adjacent to the nerve N to deliver electrical signals to the nerve N. In some embodiments, the distal end 18 of the lead 14 may include an anchor tether or strain relief cuff proximal or distal to the electrodes 20 that secures the electrode assembly to the nerve N.

During operation, the lead 14 delivers electrical signals between the IMD 12 and the electrodes 20. The electrodes 20 may be separately controlled by IMD 12. For example, energy having different magnitude, phase, and/or timing characteristics may be delivered to or from each of the electrodes 20. While the lead 14 shown includes three electrodes 20, any number of electrodes having any arrangement on the lead 14 can alternatively be employed in the system 10. Furthermore, the IMD 12 shown is merely by way of illustration, and the IMD 12 may have any configuration suitable for use in conjunction with the lead 14 and may be implanted in any suitable location in the patient's body. For example, one or more of the electrodes 20 may alternatively be configured on a pre-shaped lead body 15 that is placed into a blood vessel.

The electrodes 20 are configured for stimulation or sensing of a nerve or nerve bundle. In the embodiment shown, the distal end 18 is positioned adjacent to the vagus nerve N. The electrodes 20 may be implanted adjacent the nerve, with the IMD 12 configured to deliver energy to the electrodes 20 to stimulate the nerve. Stimulating the sympathetic and parasympathetic nervous systems can have effects on physiological parameters associated with the heart H, such as heart rate and blood pressure. The functions associated with the sympathetic and parasympathetic nervous systems are many and can be complexly integrated with each other.

The vagus nerve N has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-MI patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development or worsening of congestive heart failure (CHF) following MI. The electrodes 20 may be configured and arranged to stimulate the vagus nerve N to provide any of the physiological responses described. While the electrodes 20 are shown positioned adjacent the right vagus nerve N in FIG. 1, the electrodes 20 can be configured and arranged to stimulate the left vagus nerve N to treat other physiological and psychological conditions, such as epilepsy and depression.

In the embodiment shown, the electrodes 20 are configured as band electrodes including conductive material around a perimeter of the distal end 18 of the lead 14. When the electrodes 20 are positioned adjacent to the nerve N, the lead 14 may be configured to direct stimulation energy toward target tissue while minimizing the stimulation energy delivered to the surrounding tissue. In addition, the lead 14 may be configured to maintain its position relative to the target tissue so that the lead 14 can deliver energy to the target tissue at a consistent location. The insulative stability structures described herein facilitate directional control of stimulation energy while providing stability of the lead 14 relative to the nerve N.

Figure 2A:
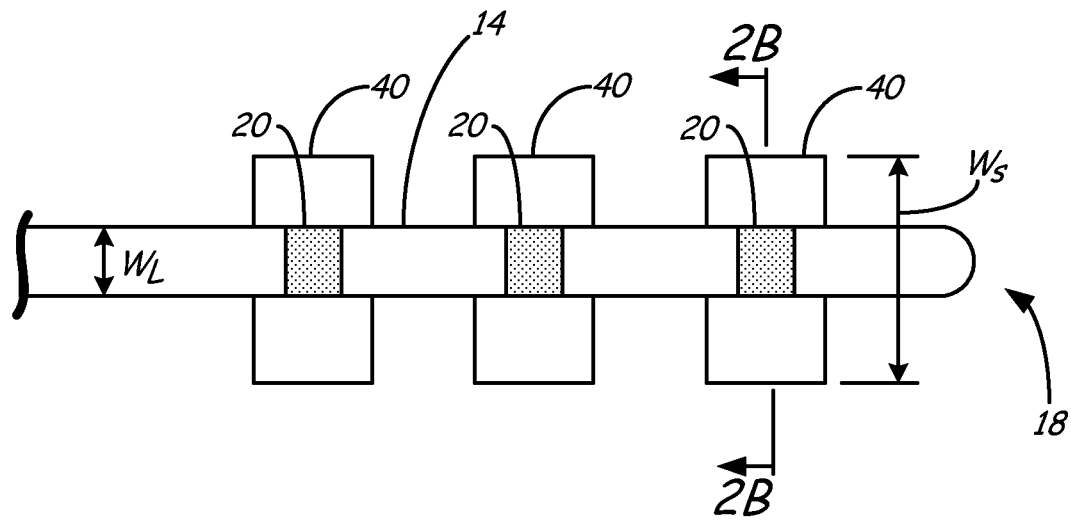
FIG. 2A is a plan view of a distal end of a lead including electrodes with an embodiment of insulative stability features attached thereto.
Figure 2B:
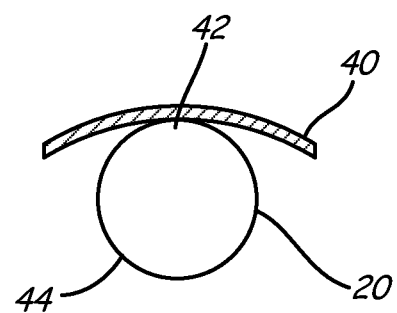
FIG. 2B is a cross-sectional view of the lead shown in FIG. 2A through an insulative stability feature.

FIG. 2A is a plan view of the distal end 18 of the lead 14 including electrodes 20 with an embodiment of insulative stability elements 40 attached thereto. FIG. 2B is a cross-sectional view of the lead 14 through line 2B-2B in FIG. 2A, illustrating the relationship between the electrodes 20 and the associated insulative stability element 40. In the embodiment shown in FIGS. 2A and 2B, the insulative stability elements 40 have a quadrangular shape, and are generally curved with respect to the electrodes 20. While insulative stability elements 40 are shown associated with each electrode 20, some of the electrodes 20 may be configured without insulative stability elements 40.

In the embodiment shown, the insulative stability elements 40 are secured to a first portion 42 of the electrodes 20 such that a second portion 44 of the electrodes 20 remain exposed. In some embodiments, the insulative stability elements 40 are chemically adhered to the electrode 20 and/or lead body 15 to secure the insulative stability elements 40 to the electrodes 20. In other embodiments, the insulative stability elements 40 are formed integrally with the lead body 15 such that lead body 15 extends over the electrode 20 along first portion 42. With this arrangement, the second portion 44 is configured to deliver electrical signals to adjacent tissue (e.g., nerve N), while the first portion 42 is insulated from surrounding tissue. This facilitates directed delivery of the stimulation energy to target tissue while preventing unwanted (i.e., extraneous) stimulation of surrounding tissue.

The lead 14 illustrated in FIG. 2A has a width $w_L$ and the insulative stability elements 40 each have a width $w_S$. The width $w_L$ of the lead 14 is transverse to the length of the lead 14, the latter of which extends from the proximal end 16 to the distal end 18. In the embodiment shown, the width $w_S$ is greater than the width $w_L$, and each insulative stability element 40 is arranged with respect to its associated electrode 20 such that the insulative stability element 40 overhangs or extends beyond the periphery of the lead 14. In some embodiments, the width $w_S$ of the insulative stability elements 40 is at least about 1.5 times greater than the width $w_L$ of the lead 14. Stated differently, the width $w_S$ of the insulative stability elements 40 may be such that the insulative stability elements 40 extend beyond the outer periphery of the lead 14 by at least about 25 percent of the width $w_S$ of the insulative elements 40.

In some embodiments, the insulative stability elements 40 are comprised of a flexible biocompatible material. Example materials that are suitable for use for the insulative stability elements 40 include, but are not limited to, silicone, polyurethane, polytetrafluoroethylene (PTFE), ethylene tetrafluoroethylene (ETFE), polyurethane, and polyester. The insulative stability elements 40 may also comprise a mesh material to encourage tissue in-growth and secure the insulative stability elements 40 to surrounding tissue. In some embodiments, the insulative stability elements 40 have a thickness in the range of about 0.1 millimeters (mm) to about 0.8 mm.

The lead 14 may be delivered to the implantation site using a catheter or introducer, for example. The insulative stability elements 40 may be collapsed around the lead body 15 to minimize the profile of the lead 14 when the lead 14 is being fed through the catheter or introducer. When the lead 14 is at the implantation site, the catheter or introducer is removed, and the insulative stability elements 40 can expand back to the pre-collapsed configuration in which the insulative stability elements 40 extend outward from the lead body 15. The insulative stability elements 40 may be reinforced with a shape memory material (e.g., Nitinol) to ensure that the insulative stability elements 40 return to their pre-implantation shape so that the insulative stability elements 40 do not cover the electrodes 20 after implantation.

When the insulative stability elements 40 return to their extended configuration, the insulative stability elements 40 urge against surrounding anatomy to stabilize the lead 14 with respect to the target tissue to be stimulated. In some embodiments, one or more of the insulative stability elements 40 may further include a tine or other protrusion extending from the major surface of the insulative stability elements to provide further stability and/or force the lead 14 toward the target tissue.

Figure 3:
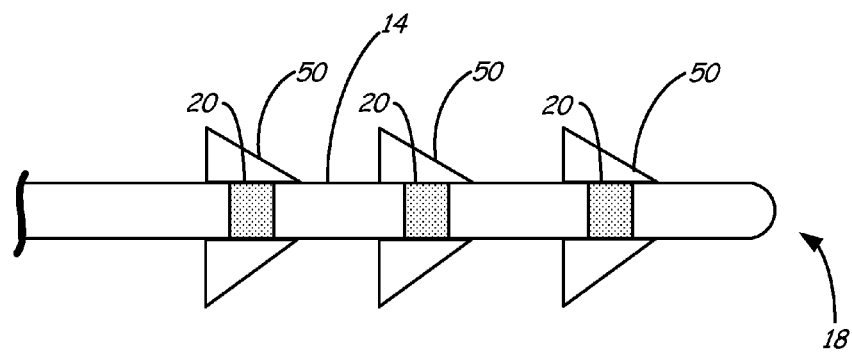
FIG. 3 is a plan view of a distal end of a lead including electrodes with another embodiment of insulative stability features attached thereto.
Figure 4:
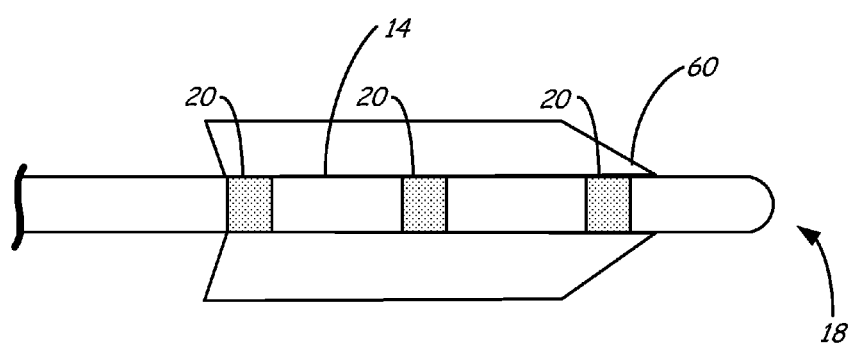
FIG. 4 is a plan view of a distal end of a lead including electrodes with a further embodiment of insulative stability features attached thereto.

The shape and configuration of the insulative stability elements 40 in FIGS. 2A and 2B are merely illustrative, and other configurations are also possible. For example, FIG. 3 illustrates an embodiment of insulative stability elements 50 having a substantially triangular shape. Each electrode 20 includes an associated triangular-shaped insulative stability element 50. As another example, FIG. 4 illustrates an embodiment of insulative stability element 60 that spans across multiple electrodes 20. The embodiments illustrated in FIGS. 3 and 4 may have similar configurations, materials, and delivery characteristics as the insulative stability element 40 discussed herein with respect to FIGS. 2A and 2B. In addition, the shapes of the insulative stability elements 40, 50, and 60 disclosed are not intended to be limiting, and other shapes are also contemplated, including rounded or polygon. The preferred stimulation direction and stability may influence the shape of the insulative stability elements.

The physical relationship between the insulative stability element 40 and electrode 20 illustrated in FIG. 2B is also merely by way of example, and other configurations are also possible. In some embodiments, the insulative stability elements may be shaped to direct the electrode into good contact with the target tissue, for example by urging against surrounding anatomy and/or orienting the lead 14 with respect to the target tissue. For example, FIG. 5A illustrates an insulative stability element 80 that contours to about half of the electrode 20 and then extends substantially perpendicular from the electrode 20 in the overhang portion. FIG. 5B illustrates an insulative stability element 80 that curves away from the electrode 20. In this embodiment, the overhanging portion of the insulative stability element 80 may press against surrounding anatomy to force the second portion 44 toward the target tissue. FIG. 5C illustrates an insulative stability element 90 that conforms to the electrode 20 and includes curved wing portions 92 in the overhang portion. FIG. 5D illustrates an insulative stability element 100 that includes a tight turn 102 near the first portion 42 that may expand when the surrounding anatomy is forced against it. Again, the illustrated embodiments are not intended to be limiting, and other cross-sectional arrangements are also possible.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. For example, while the disclosed insulation and stability features have been described with respect to a neural stimulation system, the insulation and stability features may also be employed in association with other types of leads, such as leads in a cardiac stimulation system. Accordingly, the scope of the present invention is intended to embrace all such alternatives, modifications, and variations as fall within the scope of the claims, together with all equivalents thereof.

I claim:

1. A lead assembly for an implantable medical device, the lead assembly comprising:
   a lead body having a proximal end and a distal end, wherein a length of the lead body extends from the proximal end to the distal end and a width of the lead body is transverse to the length;
   one or more electrodes disposed proximate a distal end of the lead body; and one or more insulative elements coupled to the one or more electrodes to insulate a first portion of the one or more electrodes such that a second portion of the one or more electrodes is exposed for delivering electrical signals, the one or more insulative elements each having a width greater than the width of the lead body, wherein insulative elements are collapsible during implantation, and wherein the insulative elements extend to an uncollapsed state after implantation.

2. The lead assembly of claim 1, wherein the width of the one or more insulative elements is at least about 1.5 times the width of the lead body.

3. The lead assembly of claim 1, wherein the one or more insulative elements extend beyond the width of the lead body by more than 1.0 mm.

4. The lead assembly of claim 1, wherein the one or more insulative elements are comprised of a flexible material.

5. The lead assembly of claim 1, wherein each of the one or more electrodes is a band electrode.

6. The lead assembly of claim 1, wherein each of the one or more insulative elements is associated with one of the one or more electrodes.

7. The lead assembly of claim 1, wherein at least one of the one or more insulative elements is coupled to more than one of the one or more electrodes.

8. A lead assembly for an implantable medical device, the lead assembly comprising:
a lead body having a proximal end, a distal end, a length that extends between the proximal end and distal end, and a width transverse to the length;
one or more conductors extending through the lead body and configured for connection to a pulse generator;
one or more electrodes at the distal end of the lead body electrically coupled to the one or more conductors, the one or more electrodes configured for placement adjacent to tissue to be stimulated, each of the one or more electrodes having a circumference extending around the electrode, the circumference comprising a first portion and a second portion; and
one or more insulative elements respectively coupled to the one or more electrodes to cover the first portion of the circumference of each of the one or more electrodes while the second portion of the circumference of each of the one or more electrodes remains exposed, the one or more insulative elements each having a width greater than the width of the lead body.

9. The lead assembly of claim 8, wherein the width of the one or more insulative elements is at least about 1.5 times the width of the lead body.

10. The lead assembly of claim 8, wherein the one or more insulative elements extend beyond the width of the lead body by more than 1.0 mm.

11. The lead assembly of claim 8, wherein the one or more insulative elements are comprised of a flexible material.

12. The lead assembly of claim 8, wherein insulative elements are collapsible during implantation, and wherein the insulative elements extend to an uncollapsed state after implantation.

13. The lead assembly of claim 8, wherein each of the one or more insulative elements is associated with one of the one or more electrodes.

14. The lead assembly of claim 8, wherein at least one of the one or more insulative elements is coupled to more than one of the one or more electrodes.

15. A lead assembly for an implantable medical device, the lead assembly comprising:
a lead body having a proximal end and a distal end, wherein a length of the lead body extends from the proximal end to the distal end and a width of the lead body is transverse to the length;
one or more electrodes disposed proximate a distal end of the lead body; and
one or more insulative elements coupled to the one or more electrodes such that, when the lead assembly is implanted, the one or more insulative elements are on a side of the lead body opposite tissue to be stimulated, the one or more insulative elements each having a width greater than the width of the lead body such that portions of the insulative elements extend beyond the periphery of the lead body, wherein insulative elements are collapsible during implantation, and wherein the insulative elements extend to an uncollapsed state after implantation.

16. The lead assembly of claim 15, wherein the width of the one or more insulative elements is at least about 1.5 times the width of the lead body.

17. The lead assembly of claim 15, wherein the one or more insulative elements are comprised of a flexible material.

18. The lead assembly of claim 15, wherein each of the one or more electrodes is a band electrode.

19. The lead assembly of claim 15, wherein each of the one or more insulative elements is associated with one of the one or more electrodes.

20. The lead assembly of claim 15, wherein at least one of the one or more insulative elements is coupled to more than one of the one or more electrodes.

* * * * *